United States Patent [19]

Pan et al.

[11] Patent Number: 5,199,955
[45] Date of Patent: Apr. 6, 1993

[54] M-PHENYLENEDIAMINE COUPLER AND OXIDATIVE DYE COMPOSITIONS CONTAINING SAME

[75] Inventors: Yuh-Guo Pan, Stamford; Mu-Ill Lim, Trumbell, both of Conn.; Alexander C. Chan, Mineola, N.Y.

[73] Assignee: Clairol Inc., New York, N.Y.

[21] Appl. No.: 898,652

[22] Filed: Jun. 15, 1992

[51] Int. Cl.$^5$ .............................................. A61K 7/13
[52] U.S. Cl. ......................................... 8/411; 8/405; 8/406; 8/407; 8/408; 8/410; 8/416; 424/70; 564/441; 564/442
[58] Field of Search .................... 8/405, 406, 407, 408, 8/410, 411, 416; 424/70; 564/441, 442

[56] References Cited

U.S. PATENT DOCUMENTS 4,845,294  7/1989  Konrad et al. ..................... 8/416

FOREIGN PATENT DOCUMENTS 4-122729  4/1992  Japan.

Primary Examiner—Paul Lieberman
Assistant Examiner—William S. Parks
Attorney, Agent, or Firm—Morton S. Simon

[57] ABSTRACT

1,5-diamino-2,4-bis(2,2,2-trifluoroethoxy) benzene is a novel m-phenylenediamine coupler and oxidative dye compositions containing same. Stronger dyeing intensity is afforded by use of the novel coupler of the invention.

2 Claims, No Drawings

M-PHENYLENEDIAMINE COUPLER AND OXIDATIVE DYE COMPOSITIONS CONTAINING SAME

The instant invention relates to a novel m-phenylenediamine coupler for oxidative dye compositions in the dyeing of keratinous fibers and oxidation dye compositions containing same. The invention further relates to intermediates for the production of such coupler.

1,5-Diamino-2,4-bis(2,2,2-trifluoroethoxy)benzene is a novel m-phenylenediamine coupler having the formula I.

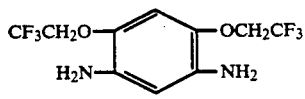

m-Phenylenediamine and its derivatives are well known as blue couplers in oxidative hair coloring. They couple with p-phenylenediamine and its derivatives to impart blue coloration to hair. Although very intense blue colors can be obtained by the use of such known blue couplers as 2,4-diaminoanisole, 2,4-diaminophenetol and 2-(2,4-diaminophenoxy)ethanol, the blue colors which result contain a red hue. This is undesirable when coloring hair black. U.S. Pat. No. 4,543,425, teaches the use of 2-(2,4-diaminophenoxy)-1,1,1-trifluoroethane to minimize this problem. However, U.S. Pat. No. 4,886,516 reports that 2-(2,4-diaminophenoxy)-1,1,1-trifluoroethane is mutagenic to salmonella thyphimurium strain TA 98.

Blue couplers, known as 2-equivalent couplers, are detailed by Corbett (J. Chem. Soc. Perkin II, 1972, 999).

U.S. Pat. No. 4,566,876 also details an invention of 2-equivalent couplers as hair dyes. Patentees disclose compounds of the formula

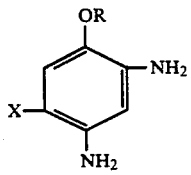

wherein X is halogen or $OR^1$; R and $R^1$ are, independently, alkyl, mono- or poly-hydroxyalkyl, alkoxyalkyl, alkylphenyl, aminoalkyl, mono- and di-alkylaminoalkyl, phenyl or phenylalkyl, except that R and $R^1$ cannot both be methyl. However, such compounds are disadvantageous in that they provide colors having red overtones. Moreover, they are sensitive to air. In point of fact, one advantage of using 2-equivalent couplers is that they undergo rapid reaction with oxidation developers without requiring excessive amounts of oxidizing agent. However, the 2-equivalent couplers, present a number of difficulties from the standpoint of chemical stability. They are difficult to isolate and therefore expensive to manufacture. The quality of the dyes deteriorates during long-term storage. Therefore, they exhibit inconsistent dyeing performance.

It is clear from the above that there is need in the art for further improvement in oxidative couplers for hair dyeing compositions.

SUMMARY OF THE INVENTION

The present inventors have found that 1,5-diamino-2,4-bis (2,2,2-trifluoroethoxy)benzene having the formula I

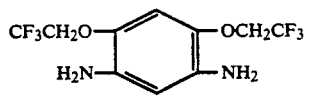

is a 2-equivalent oxidative dye coupler that is stable and, therefore, an effective component of hair dyeing compositions.

1,5-Diamino-2,4-bis(2,2,2-trifluoroethoxy)benzene (I) can be economically synthesized and isolated as a free base without difficulty. Moreover, during a six-month period of storage at room temperature, no significant deterioration of the quality of coupler (I) was observed.

The novel coupler (I) of the present invention, when combined with the developer, p-phenylenediamine, colors hair blue. Moreover, its dyeing intensity is stronger than that obtained from 2-(2,4-diaminophenoxy)-1,1,1-trifluoroethane and p-phenylenediamine. A further advantage of the novel coupler of the present invention is that when it is coupled with p-aminophenol it imparts to bleached hair a much more intense red coloration than is obtained with 2-(2,4-diaminophenoxy) 1,1,1-trifluorethane.

Coupler (I) of the present invention can be obtained by methods known in the art. For example, 1,5-dichloro-2,4-dinitrobenzene (II) is reacted with 2,2,2-trifluoroethanol and KF in the presence of TDA-1 (tris[2-methoxyethoxy)ethyl]amine) to produce the compound of the Formula (III). This substitution reaction can also be carried out by use of sodium trifluoroethoxide. Catalytic hydrogenation of compound (III) or iron reduction of same, provides compound I. The overall reaction scheme may be depicted as follows:

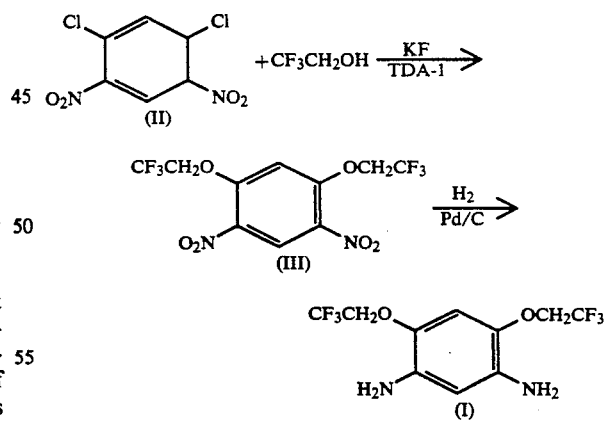

1,5-Diamino-2,4-bis(2,2,2-trifluoroethoxy)benzene (I) can be prepared in two steps from 1,5-dichloro-2,4-dinitrobenzene (II).

Substitution of compound (II) with 2,2,2-trifluoroethanol, in the presence of potassium fluoride, produces compound (III). Catalytic hydrogenation of compound (III), using Pd/C (10%) in methanol, affords compound (I).

Examples 1 and 2, which follow, are illustrative of the above depicted reaction scheme:

EXAMPLE 1

1,5-dinitro-2,4-bis(2,2,2-trifluoroethoxy) benzene(III)

A mixture of 1,5-dichloro-2,4-dinitrobenzene(II) (50g, 0.21 mol) with 8 eq of potassium fluoride (97.6g, 1.68 mol) and TDA-1 (2.50 g) in 250 ml of 2,2,2-trifluoroethanol was heated at 80° C. for 24 hours under stirring. The mixture was then poured onto crushed ice/$H_2O$. The resultant yellow precipitate was collected by filtration, washed 3 times with water, and air dried to give 73.20g (95% yield) of compound III: mp 129°–132° C.; MS m/e 364 (M+); $^1$HNMR (DMSO-$d_6$)δ 5.13 (q, 4H, J=8.7 Hz), 7.37 (s, 1H), 8.75 (s, 1H).

EXAMPLE 2

1,5-diamino-2,4-bis(2,2,2-trifluoroethoxy) benzene (I)

A mixture of 1,5-dinitro-2,4-bis (2,2,2-trifluoroethoxy)benzene(III) (30g, 82 mmol) and 3.0g of 10% Pd/C in 150 ml of methanol was hydrogenated for 2 hours under 60 psi and at room temperature. To remove the catalyst, the mixture was filtered over celite onto ice/$H_2O$, then washed several times with methanol. The desired product was precipitated from water, collected by filtration, washed three times with water, and dried to give 25.0 g (yield=100%) of compound (I): mp 109° C.; MS m/e 304 (M+); $^1$HNMR (acetone-$d_6$)δ 4.93 (q, 4H, J=9.0 Hz), 7.30 (s, 1H), 7.45 (s, 1H).

Examples 3 and 4, which follow, serve to illustrate the novel compositions of the present invention.

EXAMPLE 3

The following dye composition was prepared:

| | |
|---|---|
| Compound I (produced in Example 2) | 0.0513 g |
| $N^1N^1$-bis(2-hydroxyethyl)p-phenylene diamine sulfate | 0.04 g |
| Isopropanol | 2.00 g |
| Water | 8.00 g |
| Hydrogen peroxide (20 volume) | 10.00 g |
| | 20.0913 g |

The pH of the dye composition was adjusted to 9.5 with $NH_4OH$. The composition was then used to dye swatches of blended gray and bleached hair. The hair was soaked in the dye composition for 20 minutes, at room temperature, then rinsed with water. The hair swatches were dyed a blue-green color.

EXAMPLE 4

The following dye composition was prepared:

| | |
|---|---|
| Compound I (produced in Example 1) | 0.1396 g |
| p-Phenylenediamine | 0.04 g |
| Isopropanol | 2.00 g |
| Water | 8.00 g |
| Hydrogen Peroxide (20 volume) | 10.00 g |
| | 20.1796 g |

The pH of the dye composition was adjusted to 9.5 with $NH_4OH$. The composition was then used to dye swatches of blended gray and bleached hair, utilizing the procedure of Example 3. The composition imparted a dark blue coloration to the hair. Comparison with prior art compound:

EXAMPLE 5

(1) The following hair dye composition A was prepared:

| | |
|---|---|
| Compound I (produced in Example 2) | 0.0563 g |
| p-Phenylenediamine | 0.02 g |
| 95% Ethanol | 4.00 g |
| Water | 6.00 g |
| Hydrogen peroxide (20 volume) | 10.00 g |
| | 20.0763 g |

The pH of composition A was adjusted to 9.5 with $NH_4OH$. Composition A was then used to dye swatches of blended gray and bleached hair, utilizing the procedure of Example 3. Composition A imparted a dark blue coloration to the hair.

(2) For comparative purpose, the following composition B was prepared:

| | |
|---|---|
| 1,3-Diamino-4-(2,2,2-trifluoroethoxy) benzene | 0.0515 g |
| p-Phenylenediamine | 0.02 g |
| 95% Ethanol | 4.00 g |
| Water | 6.00 g |
| Hydrogen peroxide (20 volume) | 10.00 g |
| | 20.0715 g |

The pH of composition B was adjusted to 9.5 with $NH_4OH$. Composition B was then used to dye swatches of blended gray hair utilizing the procedure of Example 3. Composition B imparted a lighter blue coloration to the hair when compared to Example 5(1).

Hunter Tristimulus Values were determined for these swatches and are reported in Table 1 below.

TABLE 1

| | Hunter Tristimulus Values | | |
|---|---|---|---|
| | L | a | b |
| Coupler I - Example 5(1) | 12.91 | 1.15 | −3.14 |
| 1,3-Diamino-4-(2,2,2-trifluoroethoxy) benzene - Example 5(2) | 17.61 | 0.85 | −1.83 |

In the Hunter Tristimulus System: "L" is a measure of lightness and darkness (in other words, the depth of the color of the hair tress); "a" is a measure of the greenness or redness of the hair's color (as the value of "a" increases, green tonality of the hair decreases and red tonality of the hair becomes more prominent; as the value of "a" decreases, red tonality of the hair decreases and green tonality of the hair increases); "b" is a measure of the blueness or yellowness of the hair color (as the value of "b" decreases, the hair tress becomes bluer in color).

The Hunter Tristimulus values of Table demonstrate that coupler I dyes blended gray a more intense blue color than is obtained with 1,3-diamino-4-(2,2,2-trifluoroethoxy)benzene. Comparison with prior art compounds:

EXAMPLE 6

(1) The following Hair dye composition C was prepared:

| | |
|---|---|
| Compound I (produced in Example 2) | 0.0558 g |
| p-Aminophenol | 0.02 g |

| -continued | |
| --- | --- |
| 95% Ethanol | 4.00 g |
| Water | 6.00 g |
| Hydrogen peroxide (20 volume) | 10.00 g |
| | 20.0758 g |

The pH of composition C was adjusted to 9.5 with NH$_4$OH.

(2) The following hair dye composition D was prepared:

| | |
| --- | --- |
| 1,3-Diamino-4-(2,2,2-trifluoroethoxy)benzene | 0.0510 g |
| p-Aminophenol | 0.02 g |
| 95% Ethanol | 4.00 g |
| Water | 6.00 g |
| Hydrogen peroxide (20 volume) | 10.00 g |
| | 20.0710 g |

The pH of composition D was adjusted to 9.5 with NH$_4$OH

Compositions C&D were then used to dye swatches of bleached hair. The hair was soaked in the dye composition for 20 minutes, at room temperature, then rinsed with water.

Compositions C and D each imparted red coloration to the hair. However, composition C produced a more intense coloration.

Hunter Tristimulus Values were found to be as follows:

| | L | a | b |
| --- | --- | --- | --- |
| Coupler I - Example 6(1) | 14.60 | 8.27 | 3.96 |
| 1,3-Diamino-4-(2,2,2-trifluoroethoxy)benzene - Example 6(2) | 22.44 | 11.71 | 6.17 |

EXAMPLE 7

The following hair dye compositions E and F were prepared:

| | Composition E | Composition F |
| --- | --- | --- |
| Nonoxynol 4 | 10.5 g | 10.5 g |
| Nonoxynol 9 | 12.0 g | 12.0 g |
| Oleic acid | 2.0 g | 2.0 g |
| Propylene glycol | 1.5 g | 1.5 g |
| 95% Ethanol | 5.0 g | 5.0 g |
| Ethylenediamine tetraacetic acid | 1.25 g | 1.25 g |
| Sodium bisulfite | 0.18 g | 0.18 g |
| Ammonium hydroxide | 3.25 g | 3.28 g |
| Water | 13.557 g | 13.9132 g |
| Compound I | 0.5630 g | 0.2068 g |
| p-Phenylenediamine | 0.20 g | — |
| N$^1$,N$^1$-Bis(2-hydroxyethyl)-p-phenylenediamine sulfate | — | 0.20 g |
| Total | 50.0 g | 50.0 g |

Compositions E and F each had a pH of 9.9.

Hair dye composition E was mixed with 50g of 20 volume hydrogen peroxide, then allowed to react on bleached and blended gray hair for 30 minutes at room temperature. The treated tress was then rinsed with water. The hair was colored dark blue.

Hair dye composition F was mixed with 50g of 20 volume hydrogen peroxide then allowed to react on bleached and blended gray hair for 30 minutes at room temperature. The treated tress was then rinsed with water. The hair was colored a blue green shade.

What is claimed is:

1. 1,5-Diamino-2,4-bis(2,2,2-trifluoroethoxy) benzene.

2. In an oxidation hair dye composition containing a primary intermediate and a coupler, the improvement comprising 1,5-diamino-2,4-bis(2,2,2-trifluoroethoxy) benzene is the coupler.

* * * * *